United States Patent [19]
Garcia et al.

[11] Patent Number: 6,162,178
[45] Date of Patent: Dec. 19, 2000

[54] ULTRASONIC TRANSDUCER OFF-APERTURE CONNECTION

[75] Inventors: Rizza A. Garcia, Newark; Dennis M. Mendoza, Tracy, both of Calif.

[73] Assignee: Scimed Life Systems, Inc., Maple Grove, Minn.

[21] Appl. No.: 09/127,252

[22] Filed: Jul. 31, 1998

[51] Int. Cl.[7] ........................................... A61B 8/12
[52] U.S. Cl. .................... 600/459; 600/462; 29/25.35
[58] Field of Search .................... 600/437, 447, 600/459, 463, 466, 472; 367/140, 152; 310/327, 358, 311–319; 29/25.35; 73/642

[56] References Cited

U.S. PATENT DOCUMENTS

| | | | |
|---|---|---|---|
| 5,000,185 | 3/1991 | Yock | 600/459 |
| 5,701,901 | 12/1997 | Lum et al. | 128/662 |

*Primary Examiner*—Francis J. Jaworski
*Assistant Examiner*—Ali M. Imam
*Attorney, Agent, or Firm*—Lyon & Lyon LLP

[57] ABSTRACT

An ultrasonic transducer assembly includes a transducer mounted in a housing, the transducer including a piezoelectric element and respective matching and backing layers formed on the opposite sides thereof, the transducer mounted in the housing encapsulated with a non-conductive potting material. A portion of the matching layer is removed, e.g., by etching, to expose a portion of an underlying electrode formed between the piezoelectric element and the matching layer. A portion of the non-conductive potting material between the etched portion of the matching layer and a signal wire disposed in the housing is also removed. The respective voided portions of the matching layer and non-conductive potting material are filled with an electrically conductive matching material to electrically couple the electrode, and, thus, the piezoelectric element, to the signal wire.

21 Claims, 5 Drawing Sheets

ULTRASONIC TRANSDUCER OFF-APERTURE CONNECTION

FIELD OF THE INVENTION

This invention relates generally to the manufacture of ultrasonic transducers, and more particularly to a method of optimizing the performance characteristics of ultrasonic transducers used in ultrasonic imaging devices.

BACKGROUND

Currently, ultrasonic imaging devices are used to diagnose body tissue surrounding a body cavity, such as, e.g., the wall of a blood vessel. One type of an ultrasonic imaging device includes an invasive catheter tube with an internally disposed rotatable imaging core, the imaging core including a drive cable having a distally mounted transducer that is situated in an acoustic imaging window provided at a distal end of the catheter tube. The transducer is electrically coupled to a signal generator/processor via signal wires disposed in the drive cable. To further facilitate transmission of ultrasonic energy, the imaging window of the catheter tube is filled with an aqueous solution, thereby immersing the distally mounted ultrasonic transducer. An example of such a device is disclosed in U.S. Pat. No. 5,000,185.

When the distal end of the ultrasonic imaging catheter, and thus the ultrasonic transducer, is placed adjacent the body tissue to be diagnosed, the signal generator/processor transmits an electrical output signal via the signal wires electrically stimulating the ultrasonic transducer. As a result, the ultrasonic transducer emits ultrasonic energy, which is transmitted through the aqueous solution filled acoustic window and into the surrounding tissue. As the ultrasonic transducer is electrically stimulated, the drive cable is rotated at a high speed, thereby rotating the attached ultrasonic transducer and causing the ultrasonic energy to be transmitted into a 360° circumferential portion of the surrounding tissue.

A portion of the ultrasonic energy is reflected from the surrounding tissue back to the ultrasonic transducer, stimulating the ultrasonic transducer to produce a response electrical signal, which is transmitted back to the signal generator/processor via the signal wires. The response signal is interpreted by the signal processor and translated into a 360° image slice of the surrounding tissue, which can be seen by an attending physician on a monitor. From this image, the composition and physical characteristics of the surrounding tissue can be determined.

As depicted in FIG. 1, a typical ultrasonic transducer 10 includes a piezoelectric element 12, which is the active element that emits ultrasonic energy in response to electrical stimulation originating from a signal generator (not shown). The ultrasonic transducer 10 further includes a matching layer 14 and a backing layer 16, which are formed on opposite sides of the piezoelectric element 12. The matching layer 14 allows passage of ultrasonic energy therethrough. The backing layer 16 reflects and attenuates the ultrasonic energy, thereby facilitating the focussed and unidirectional emission of the energy 22 from the transducer 10 perpendicular to the surface of the matching layer 14. The ultrasonic energy 22 is then transmitted through an aqueous solution 20 in which the ultrasonic transducer 10 is immersed, through an acoustic window (not shown), and into the surrounding tissue (also not shown). The ultrasonic transducer 10 further includes first and second electrodes 18 and 19 formed of electrically conductive material consisting of gold, chrome, nickel or a combination thereof (thickness exaggerated in FIG. 1) for purposes of facilitating electrical connection between the piezoelectric element 12 and a positive, or power signal wire 32, and a negative, or ground signal wire (shown in FIG. 2).

Referring to FIGS. 2 and 3, a known imaging core 24 includes a drive cable 26 with a distally mounted transducer assembly 28. The transducer assembly 28 includes an electrically conductive transducer housing 30 in which the transducer 10 is mounted. The ultrasonic transducer 10 is electrically coupled to a signal generator (not shown) via the power signal wire 32 and the ground signal wire (not shown).

Using a presently known technique, the transducer 10 is mounted in the transducer housing 30, such that the backing layer 16 is in electrical contact with the transducer housing 30, and the matching layer 14 is electrically isolated from the transducer housing 28. The transducer 10 is then fixably bonded to the transducer housing 30. The ground signal wire is welded to drive cable 26 (connection not shown), which is in electrical contact with the transducer housing 30, thereby providing electrical contact with the backing layer 16.

To electrically connect the power signal wire 32 to the ultrasonic transducer 10, a portion 36 of the matching layer 14 (shown in phantom in FIG. 2) is removed, such as, e.g., by etching, to expose the surface of the first electrode 18. The power signal wire 32 is then connected to the exposed surface of the first electrode 18. Electrically conductive material 38 is then formed over the exposed surface of the first electrode 18 to ensure an integral connection between the power signal wire 32 and the first electrode 18. The ultrasonic transducer 10 and the respective power signal wire 32 and ground signal wire (not shown) 32 are encapsulated with a non-conductive material to form a non-conductive potting 40, which ensures electrical isolation between the power signal wire 32 and the ground signal wire.

Although such an ultrasonic transducer mounting and electrical connection technique generally results in an imaging core of relatively high quality, as seen in FIG. 4, disposition of the power signal wire 32 above the piezoelectric element 12 creates a portion 42 on the aperture 44 (i.e., surface area) of the transducer 10, resulting in a disturbance in the distribution of energy 46 over the aperture 44, which reduces the performance characteristics of the transducer 10. Further, the effect of the disturbance varies from one ultrasonic transducer to the next, resulting in inconsistent performance characteristics among identically rated transducers.

In addition, although the matching layer 14 of the transducer 10 is manufactured to a calculated thickness to provide an ultrasonic transducer with theoretically optimized performance characteristics (typically one-quarter wavelength with respect to a specific operating frequency), manufacturing tolerances result in transducers having performance characteristics that vary from these calculated performance characteristics.

Thus, it would be desirable to provide an electrical signal connection to the ultrasonic transducers 10 in a manner resulting in more consistent and optimized performance characteristics.

SUMMARY OF THE INVENTION

The present invention is directed to a method of manufacturing ultrasonic imaging assemblies whereby an ultrasonic transducer is electrically coupled to a signal wire by forming a bridge consisting of an electrically conductive matching material disposed between a piezoelectric element of the ultrasonic transducer and the signal wire.

In a preferred method carried out in accordance with the present invention, an ultrasonic transducer comprising a matching layer and backing layer formed on opposite sides of a piezoelectric element is fixably mounted in a transducer housing. The transducer housing has first and second leads or conductors disposed therein. The first lead can be one of a power signal wire and a ground signal wire, and the second lead can be the other of the power signal wire and the ground signal wire. The second lead is electrically coupled to the backing layer by a conventional approach.

To create the electrical connection between the first lead and the matching layer side of the piezoelectric element, a portion of the matching layer is removed, such as, e.g., by etching, to create a void in the matching layer. The void is preferably deep enough to expose an electrode, such as, e.g., a highly electrically conductive layer comprising of gold, chrome, nickel or a combination thereof, disposed on the surface of the piezoelectric element. An electrically conductive matching material is then formed in the matching layer void and extended to the first lead to thereby form an electrically conductive matching bridge. The ultrasonic transducer and the respective leads are encapsulated with a non-conductive material to ensure proper electrical isolation between the respective leads.

Other and further objects, features, aspects, and advantages of the present invention will become better understood with the following detailed description of the accompanying drawings.

BRIEF DESCRIPTION OF THE DRAWINGS

The drawings illustrate both the design and utility of preferred embodiments of the present invention, in which.

DETAILED DESCRIPTION OF THE PREFERRED EMBODIMENTS

Figure 1:
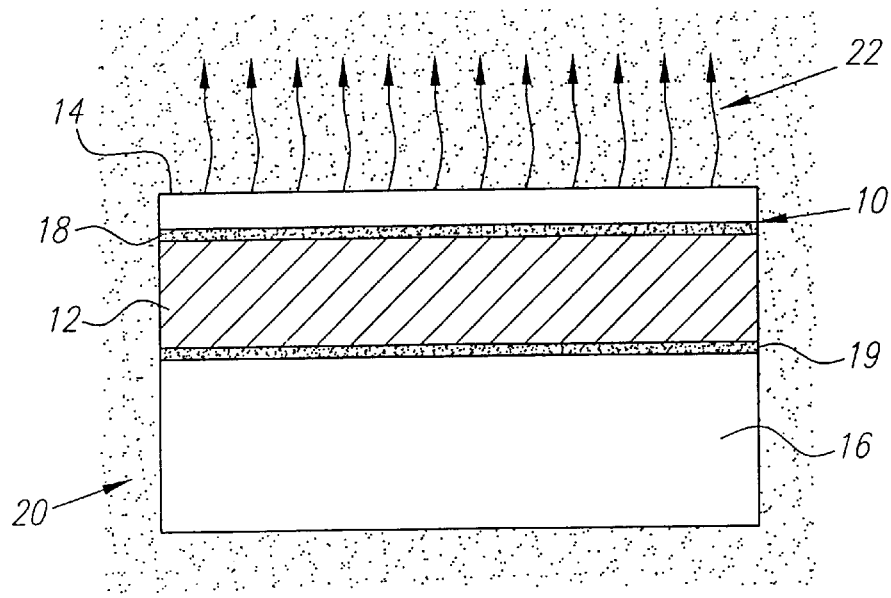
FIG. 1 is a side view of a prior art ultrasonic transducer.
Figure 2:
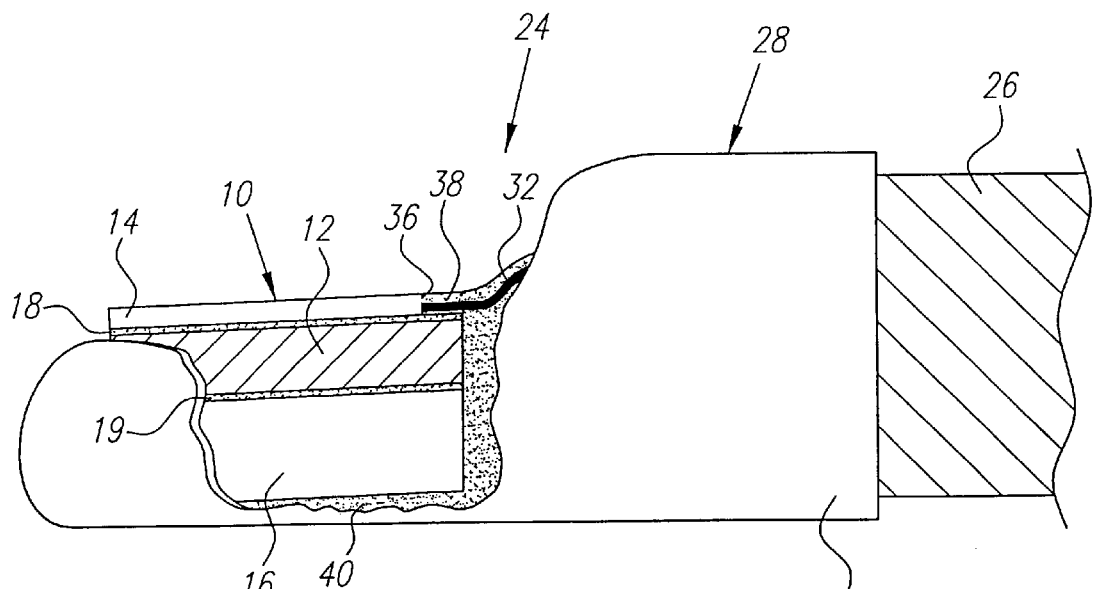
FIG. 2 is a cut away, partial side view of a prior art imaging core housing the transducer of FIG. 1.
Figure 3:
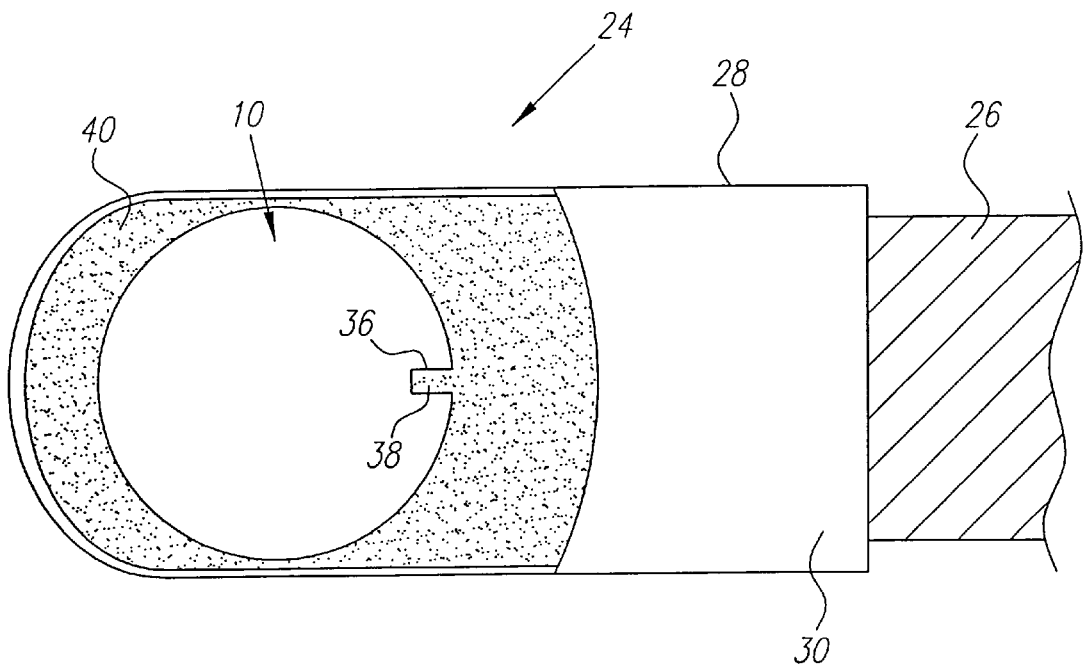
FIG. 3 is a cut away, partial top view of the imaging core of FIG. 2.
Figure 4:
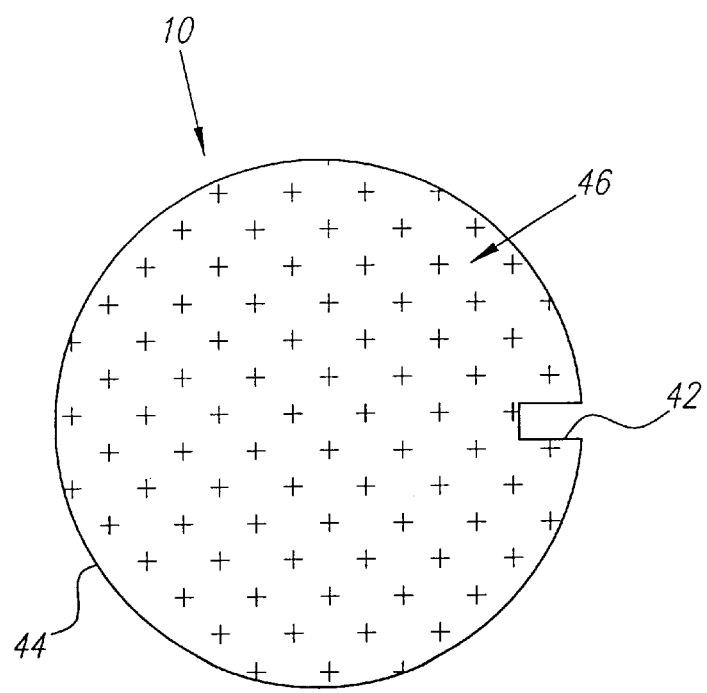
FIG. 4 is a top view of an aperture of the ultrasonic transducer imaging core in FIG. 2, depicting an ultrasonic energy distribution.
Figure 5:
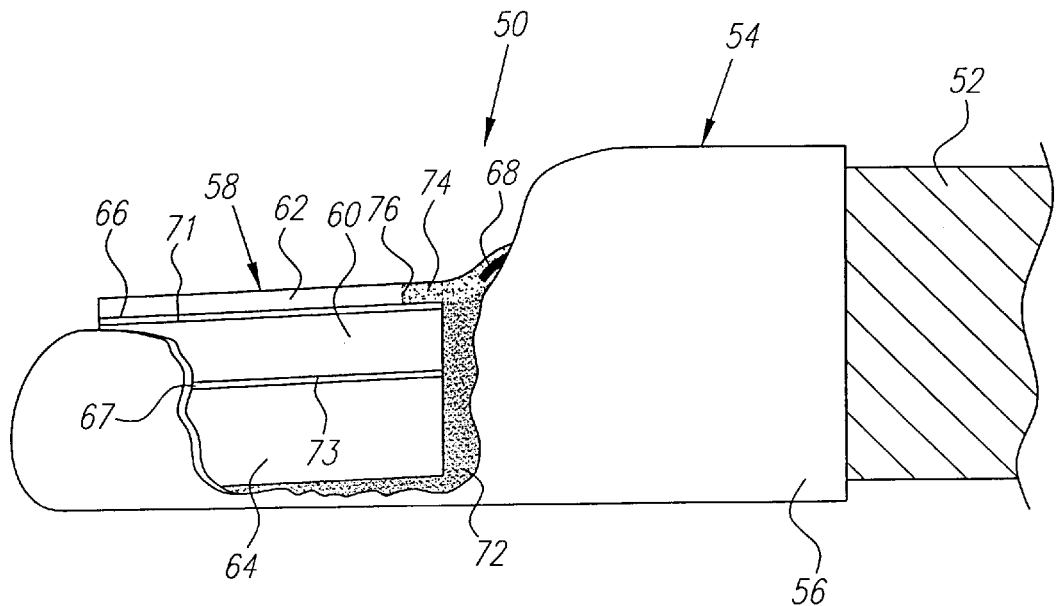
FIG. 5 is a cut away, partial side view of a preferred imaging core constructed in accordance with the present invention.
Figure 6:
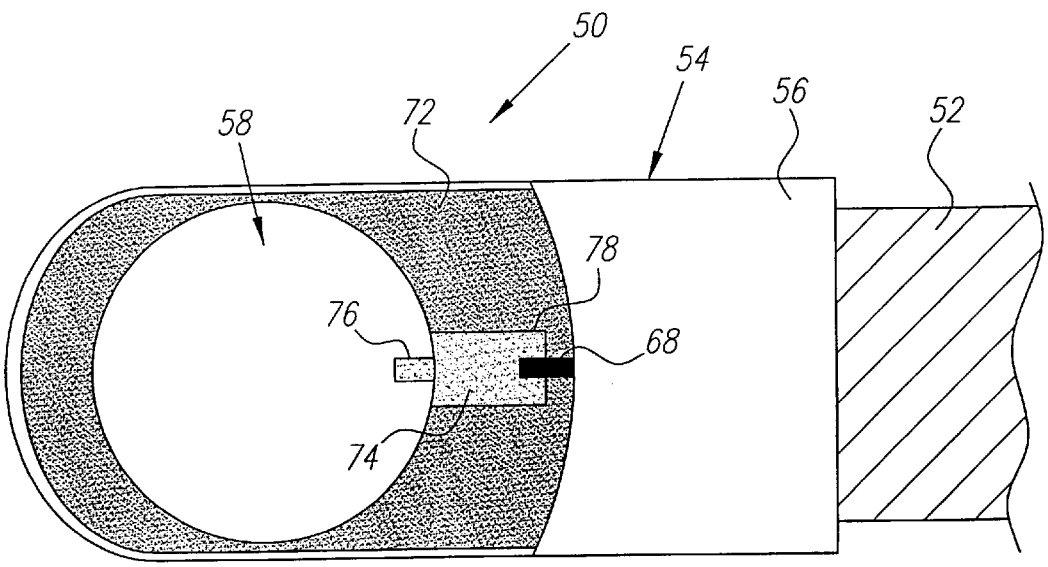
FIG. 6 is a partial top view of the imaging core of FIG. 5.
Figure 7:
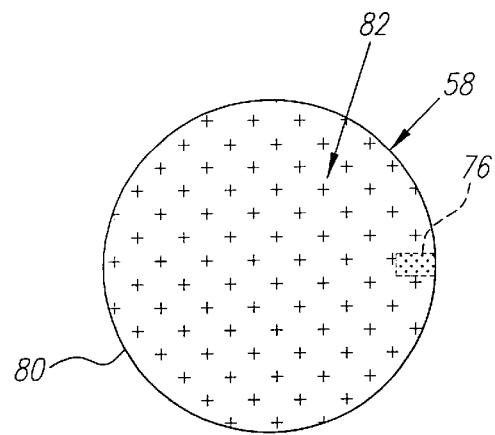
FIG. 7 is a top view of an aperture of the ultrasonic transducer mounted in the imaging core in FIG. 5, depicting an ultrasonic energy distribution.

With reference to FIGS. 5–7, an imaging core 50 constructed in accordance with a preferred method of the present inventions is disclosed. As shown in FIGS. 5 and 6, the imaging core 50 comprises a rotatable drive cable 52 and an ultrasonic transducer assembly 54. The ultrasonic transducer assembly 54 is suitably mounted, such as by, e.g., welding, to the distal end of the drive cable 52.

The ultrasonic transducer assembly 54 comprises an electrically conductive ultrasonic transducer housing 56 and an ultrasonic transducer 58. The ultrasonic transducer 58 is suitably bonded with an adhesive, such as, e.g., epoxy, into the ultrasonic transducer housing 56. The ultrasonic transducer 58 includes a piezoelectric element 60, a matching layer 62 and a backing layer 64. The respective matching and backing layers 62 and 64 are formed on a front side 71 and a back side 73 of the piezoelectric element 60. The matching layer 62 is composed of a suitable acoustically conductive material, such as, e.g., silver epoxy; and the backing layer 64 is composed of a suitable acoustically attenuative material, such as, e.g., tungsten loaded epoxy. The ultrasonic transducer 58 further includes first and second electrodes 66 and 67, such as, e.g., highly electrically conductive layers comprising of gold, chrome, nickel or a combination thereof, respectively formed between the piezoelectric element 60 and the matching layer 62, and the piezoelectric element 60 and the backing layer 64. It should be noted that the matching layer 62 can comprise multiple layers of material having differing acoustic impedances to, such as, e.g., improve the acoustic performance of the ultrasonic transducer 58, without straying from the principles taught by the present invention.

The imaging core 50 further includes a power signal wire 68 and a ground signal wire (not shown), which extend from a proximally located signal generator (not shown), through the drive cable 52, and into the ultrasonic transducer housing 56. It should be noted that this invention is not limited to the use of signal wires, and any lead or conductor adapted to deliver a signal can be used without straying from the principles taught by this invention. The power signal wire 68 and ground signal wire can encompass any lead or conductor that is adapted to deliver a signal. The power signal wire 68 is electrically coupled to the front side 71 of the piezoelectric element 60, and the ground signal wire is electrically coupled to the back side 73 of the piezoelectric element 60, thereby electrically coupling the signal generator to the ultrasonic transducer 58 and allowing the signal generator to transmit to and receive electrical signals from the ultrasonic transducer 58. It should be noted that the polarity of the power signal wire 68 and ground signal wire may also be reversed, i.e., the front side 71 of the piezoelectric element 60 may be electrically coupled to the ground signal wire and the back side 73 of the piezoelectric element 60 may be electrically coupled to the power signal wire 68.

To provide an electrical connection to the back side 73 of the piezoelectric element 60, the ground signal wire is welded to the drive cable 52, which is in electrical contact with the ultrasonic transducer housing 56. As will be discussed in further detail below, an electrical connection is provided to the front side 71 of the piezoelectric element 60 by electrically coupling the power signal wire 68 to the first electrode 66.

To ensure electrical isolation between the two power and back sides 71 and 73 of the piezoelectric element 60, the ultrasonic transducer 58 is mounted in the ultrasonic transducer housing 56, such that the backing layer 64 is in electrical contact with the ultrasonic transducer housing 56 and the matching layer 62 and first electrode 66 are not in electrical contact with the ultrasonic transducer housing 56. In addition, the ultrasonic transducer 58 and the power signal wire 68 are encapsulated with a non-conductive material, such as, e.g., U-V epoxy, creating a non-conductive potting 72 in the ultrasonic transducer housing 56. Encapsulation also aids in maintaining the structural integrity of the ultrasonic transducer assembly 54.

The power signal wire 68 is electrically coupled to the front side 71 of the piezoelectric element 60 by extending an electrically conductive matching bridge 74 from the piezoelectric element 60 to the power signal wire 68. In particular, a portion of the matching layer 62 adjacent the power signal wire 68 is removed, i.e., by etching, to create a void 76 (shown in phantom in FIG. 5) therein. Preferably, the matching layer 62 is etched deep enough to expose the underlying first electrode 66. The matching layer void 76, and thus, the portion of the exposed first electrode 66, is encapsulated with electrically conductive matching material to form one end of the electrically conductive matching bridge 74. The electrically conductive matching material has an acoustic impedance that is substantially equal to that of the matching layer 62. The electrically conductive matching material is then bridged across to the power signal wire 68 to form the center portion of the electrically conductive matching bridge 74. Lastly, the power signal wire 68 is encapsulated with the electrically conductive matching material forming the other end of the electrically conductive matching bridge 74. To facilitate bridging of the electrically conductive matching material, a portion of the non-conductive potting 72 between the matching layer void 76 and the power signal wire 68 can be etched to create a void 78 therein. The non-conductive potting void 78 can then be filled in with the electrically conductive matching material to form the center portion of the electrically conductive matching bridge 74.

Because the electrically conductive matching bridge 74 is formed of a material having an acoustic impedance that is substantially similar to that of the matching layer 62, the ultrasonic transducer 58 has an aperture 80 that minimizes the disturbance at the matching layer void 76, as shown in FIG. 7. To ensure that the ultrasonic transducer 58 emits a substantially uniform ultrasonic energy distribution 82 across the aperture 80, the acoustic impedance of the electrically conductive matching bridge 74 is similar to that of the matching layer 62. For instance, both the matching layer 62 and the electrically conductive matching bridge 74 can be composed of silver epoxy. The acoustic impedance of the electrically conductive matching bridge 74 can vary from that of the matching layer 62 without straying from the principles taught by this invention.

While the preferred method of mounting and electrical connection of an ultrasonic transducer has been described above with respect to a single ultrasonic transducer bearing rotatable imaging core, similar mounting and electrical connection procedures can be performed on other types of imaging cores, such as, e.g., a non-rotatable imaging core having a distally mounted array of ultrasonic transducers.

Figure 8:
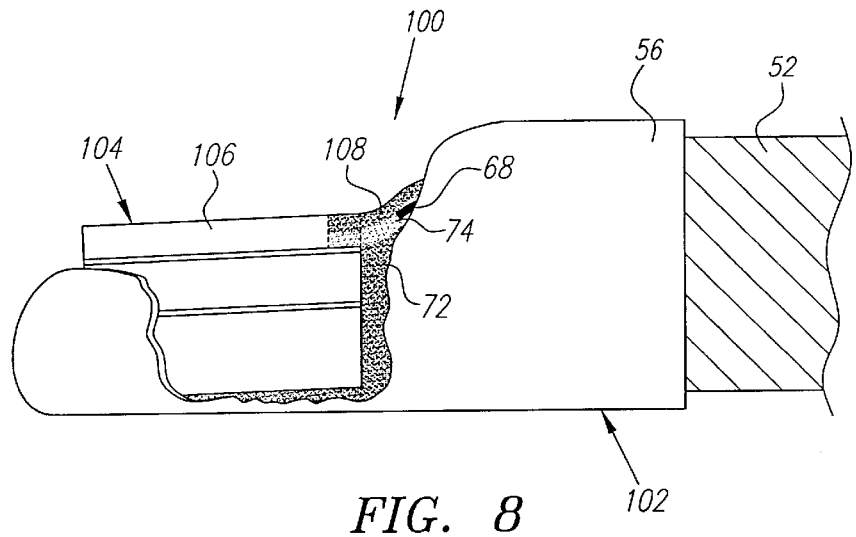
FIG. 8 is a cut away, partial side view of another preferred imaging core constructed in accordance with the present invention.
Figure 9:
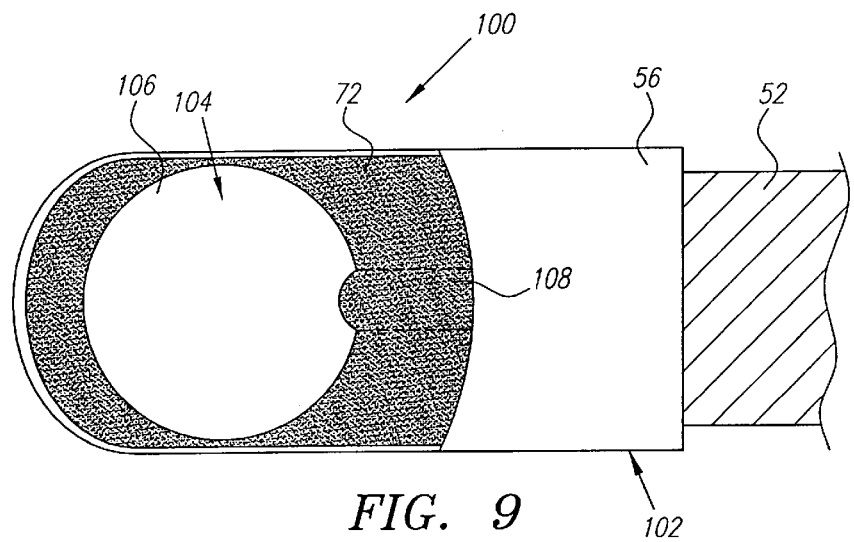
FIG. 9 is a partial top view of the imaging core of FIG. 8.
Figure 10:
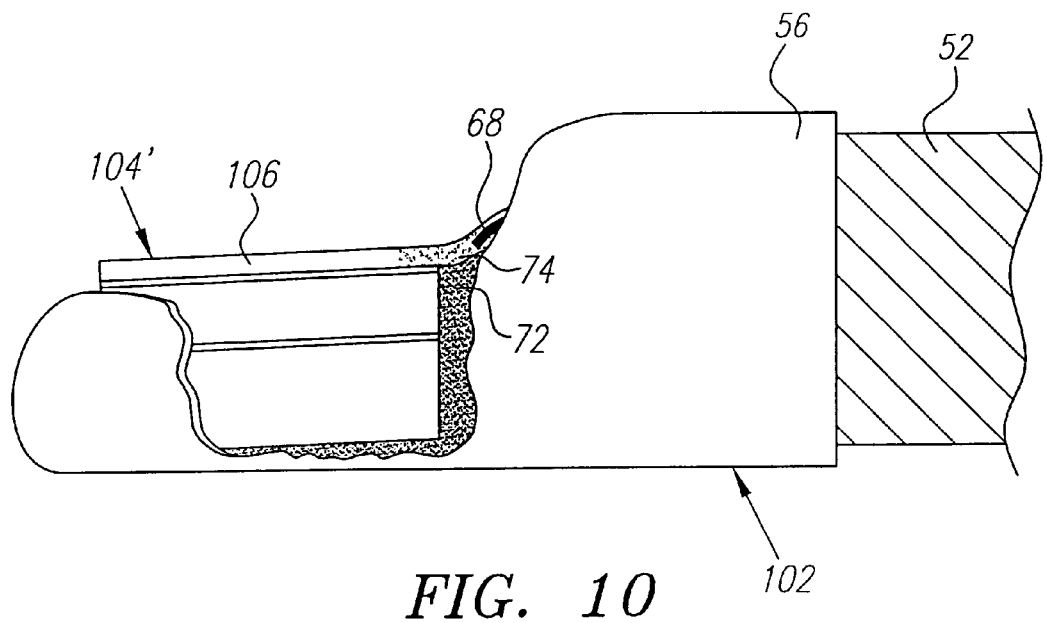
FIG. 10 is a cut away, partial side view of the imaging core of FIG. 8, wherein the ultrasonic transducer has been optimized.
Figure 11:
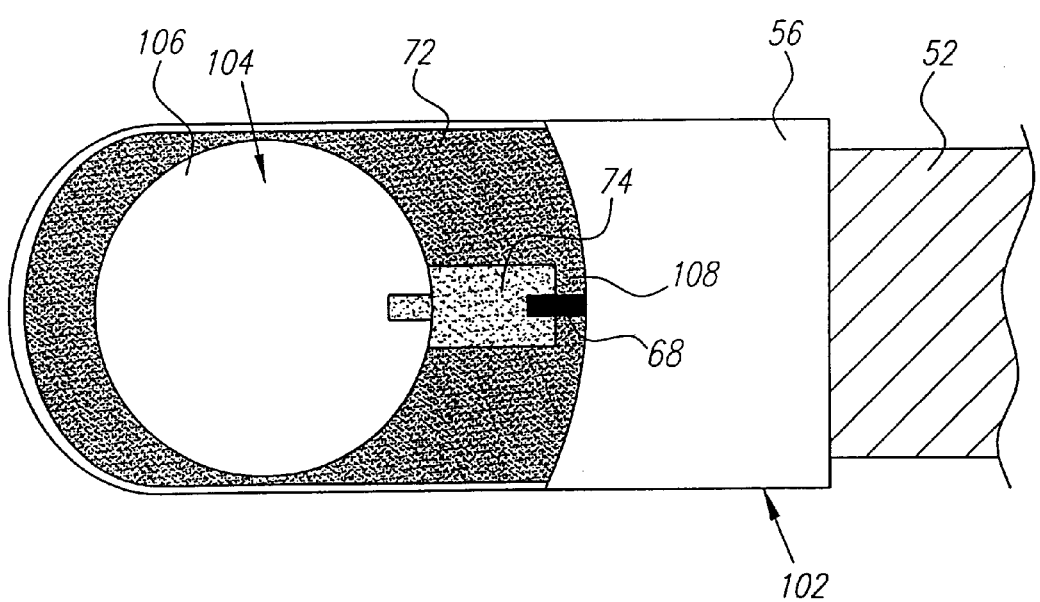
FIG. 11 is a partial top view of the imaging core of FIG. 10.

With reference to FIGS. 8–11, an imaging core 100 constructed in accordance with another preferred method of the present inventions is disclosed. As shown in FIGS. 8 and 9, an imaging core 100 comprises a distally mounted ultrasonic transducer assembly 102 and the drive cable 52. The imaging core 100, including the ultrasonic transducer assembly 102, is created in much the same manner as the imaging core 50 disclosed above, and to the extent that the imaging core 100 includes elements that are similar to those of the imaging core 50, the same reference numerals have been used.

The ultrasonic transducer assembly 102 includes the ultrasonic transducer housing 56 having mounted therein an unoptimized ultrasonic transducer 104 with an untuned matching layer 106. That is, the matching layer 106 is thicker than about one quarter wavelength with respect to the operating frequency at which the unoptimized ultrasonic transducer 104 is to perform.

The unoptimized ultrasonic transducer 104 is alternately tested and ablated to ultimately transform the unoptimized ultrasonic transducer 104 into a fully optimized ultrasonic transducer 104' (shown in FIGS. 10 and 11), the details of which are disclosed in co-pending application Ser. No. 09/127,694, entitled "Method of Tuning Ultrasonic Transducer Matching Layer," and filed concurrently herewith, which is fully incorporated herein by reference. Preferably, prior to blasting, the ultrasonic transducer assembly 102 further includes a nonconductive protective coating 108 made of a non-conductive material, which encapsulates the electrically conductive matching bridge 74. In this case, the protective non-conductive coating 108 is coincidentally ablated during the ablation procedure, thereby minimizing ablation of the electrically conductive matching bridge 74.

While preferred embodiments have been shown and described, it will be apparent to one of ordinary skill in the art that numerous alterations may be made without departing from the spirit or scope of the invention. Therefore, the invention is not to be limited except in accordance with the following claims.

What is claimed:

1. An ultrasonic transducer assembly, comprising:
   a transducer housing;
   an ultrasonic transducer mounted in the housing, the transducer comprising a piezoelectric element and a matching layer formed on the piezoelectric element;
   a first lead disposed in the housing; and
   an electrically conductive matching bridge disposed between the first lead and the piezoelectric element.

2. The ultrasonic transducer assembly of claim 1, wherein the matching layer includes a void, the bridge substantially filling the void.

3. The ultrasonic transducer assembly of claim 2, further comprising an electrode disposed between the piezoelectric element and the matching layer, the matching layer void exposing a portion of the electrode, the bridge electrically coupling the first lead to the piezoelectric element via the electrode.

4. The ultrasonic transducer assembly of claim 3, wherein the electrode comprises an electrically conductive material selected from the group consisting of gold, chrome, nickel or a combination thereof.

5. The ultrasonic transducer assembly of claim 1, wherein the matching layer has a first acoustic impedance, and wherein the bridge has a second acoustic impedance substantially equal to the first acoustic impedance.

6. The ultrasonic transducer assembly of claim 1, wherein the matching layer and bridge comprise the same material.

7. The ultrasonic transducer assembly of claim 6, wherein the matching layer and the bridge each comprises silver epoxy.

8. The ultrasonic transducer assembly of claim 1, wherein the matching layer has a first acoustic impedance, and wherein the bridge has a second acoustic impedance substantially different from the first acoustic impedance.

9. The ultrasonic transducer assembly of claim 1, further comprising a second lead wire, wherein the ultrasonic transducer further comprises a backing layer formed on the piezoelectric element opposite the matching layer, with the second lead electrically coupled to the backing layer.

10. The ultrasonic transducer assembly of claim 9, wherein the housing is electrically conductive, the matching layer is electrically isolated from the housing, the backing layer is electrically coupled to the housing, and the second lead is operably connected to the transducer housing.

11. An ultrasonic transducer assembly, comprising:

a transducer housing;

an ultrasonic transducer mounted in the housing, the transducer comprising a piezoelectric element and a matching layer formed on the piezoelectric element, a surface of the matching layer defining an aperture of the transducer;

a first signal wire disposed in the housing; and an electrically conductive matching bridge disposed between the signal wire and the piezoelectric element, wherein the signal wire is disposed outside the aperture.

12. The ultrasonic transducer assembly of claim 11, further comprising a second signal wire, wherein the ultrasonic transducer further comprises a backing layer formed on the piezoelectric element opposite the matching layer, with the second signal wire electrically coupled to the backing layer.

13. The ultrasonic transducer assembly of claim 11, wherein the matching layer and bridge comprise the same material.

14. The ultrasonic transducer assembly of claim 13, the matching layer and the bridge each comprising silver epoxy.

15. A method of constructing an ultrasonic transducer assembly, comprising:

fixably mounting an ultrasonic transducer in a transducer housing, the transducer including a piezoelectric element and a matching layer formed on the piezoelectric element, the housing including a signal wire;

forming a void in the matching layer; and encapsulating an area including the matching layer void and a portion of the signal wire with an electrically conductive matching material.

16. The method of claim 15, wherein the transducer further includes an electrode disposed between the matching layer and piezoelectric element, and wherein forming the void in the matching layer comprises exposing a portion of the highly electrically conductive material.

17. The method of claim 15, wherein the matching layer void is formed by etching the matching layer.

18. The method of claim 15, further comprising the steps:

encapsulating the transducer and signal wire with a non-conductive potting material; and forming a void in a portion of the non-conductive potting material disposed between the matching layer void and the signal wire, wherein the encapsulated area includes the non-conductive potting material void.

19. The method of claim 15, wherein the matching layer and matching material have substantially similar acoustic impedances.

20. The method of claim 15, wherein the matching layer and matching material have substantially different acoustic impedances.

21. The method of claim 15, further comprising encapsulating the matching material with a second layer of nonconductive potting material, and ablating the second layer of non-conductive potting to expose the matching material.

* * * * *